US008500782B2

(12) United States Patent
Kovach et al.

(10) Patent No.: US 8,500,782 B2
(45) Date of Patent: Aug. 6, 2013

(54) SEMI-DYNAMIC FIXATION PLATE SYSTEM

(75) Inventors: Matthew Kovach, Steamboat Springs, CO (US); David W. Wimberley, Houston, TX (US); Scott Leary, San Diego, CA (US); Paul Weaver, Douglassville, PA (US); Andrea Peukert, Tuttlingen (DE)

(73) Assignee: Aesculap Implant Systems, LLC, Center Valley, PA (US)

( * ) Notice: Subject to any disclaimer, the term of this patent is extended or adjusted under 35 U.S.C. 154(b) by 264 days.

(21) Appl. No.: 12/841,531

(22) Filed: Jul. 22, 2010

(65) Prior Publication Data

US 2012/0022593 A1    Jan. 26, 2012

(51) Int. Cl.
    *A61B 17/70*      (2006.01)
    *A61B 17/86*      (2006.01)
    *A61B 17/88*      (2006.01)

(52) U.S. Cl.
    USPC ............ 606/280; 606/289; 606/291; 606/305

(58) Field of Classification Search
    USPC ............ 606/70–71, 280–299, 307, 305, 301, 606/300, 902
    See application file for complete search history.

(56) References Cited

U.S. PATENT DOCUMENTS

| | | |
|---|---|---|
| 2002/0120273 A1* | 8/2002 | Needham et al. ............... 606/61 |
| 2003/0074001 A1 | 4/2003 | Apfelbaum et al. |
| 2004/0030336 A1* | 2/2004 | Khanna ........................... 606/61 |
| 2006/0122604 A1* | 6/2006 | Gorhan et al. .................. 606/69 |
| 2006/0122605 A1* | 6/2006 | Suh et al. ........................ 606/69 |
| 2006/0167456 A1* | 7/2006 | Johnston et al. ................ 606/69 |
| 2009/0192549 A1* | 7/2009 | Sanders et al. ................ 606/280 |

FOREIGN PATENT DOCUMENTS

EP             995404 A1 *    4/2000

* cited by examiner

*Primary Examiner* — Todd Manahan
*Assistant Examiner* — Marcela I Shirsat
(74) *Attorney, Agent, or Firm* — RatnerPrestia (57) ABSTRACT

A fixation plate system includes a plate with elongated slots, and first and second anchors for attaching the plate to vertebrae. The first and second anchors have different head configurations that are selected by the surgeon to control how settlement occurs at each fused segment. The head of the first fastener is insertable in any of the slots and resists translation. The head of the second fastener is insertable in any of the slots in free sliding engagement to allow translation of the head in that slot. In one method of use, the surgeon selects a segment where settling needs to be limited, and uses the first fastener to fix the plate near the segment and limit settling at that segment. The first and second fasteners have a built-in spring that assists in securing the fasteners in the plate.

18 Claims, 8 Drawing Sheets

SEMI-DYNAMIC FIXATION PLATE SYSTEM

FIELD

This disclosure relates generally to fixation plate assemblies for treating the spine, and more particularly to fixation plate assemblies that stabilize the position of vertebrae after fusion while allowing some relative movement of vertebrae as the vertebrae settle.

BACKGROUND

Spinal discs provide support between adjacent vertebrae in a spinal column. Over time, discs can rupture, degenerate or protrude outside of their normal space as a result of injury, degradation or disease. In such cases, the condition of the disc can be weakened or compromised to the point that the intervertebral space around the disc collapses. Changes in disc shape can cause the spine to lose its normal curvature, create impingement of nerves in the disc space, and result in chronic back pain.

A number of surgical procedures can be performed to treat damaged or degenerated discs. In one procedure, the disc is removed, and the remaining adjacent vertebrae are fused together by graft material. Graft material may be contained in an interbody implant or cage. An elongated fixation plate is then placed over the segment or segments being fused. The fixation plate includes openings to receive bone screws. Bone screws are driven through the openings and into vertebrae surrounding the segment or segments to secure the plate over the fused segments. Once secured, the plate assists in controlling relative movement of vertebrae as the vertebrae are fused together.

It is common for vertebrae to settle and compress together at segments being fused. In some approaches, a certain amount of settling and compression is desirable to maintain the graft material under constant load to promote bone growth and stronger fusion between vertebrae. Therefore, a number of plate constructs allow the bone screws to translate relative to the plate to allow the vertebrae to settle. For example, U.S. Pat. No. 6,533,786 to Needham discloses a three-level plate having a pair of circular holes at one end of the plate, and multiple pairs of elongated slots along the rest of the plate. The circular holes and slots are adapted to receive bone screws. Screw translation is regulated as a function of the shape and size of the holes or slots. Once the plate is anchored to vertebrae, the circular holes prevent any bone screw translation of the plate at the one end of the plate, fixing the one end of the plate to the underlying vertebral body. The elongated slots permit limited translation of bone screws at other levels, allowing settlement at those segments. Because one end of the plate is fixed, the levels away from the fixed end settle in one direction toward the fixed end of the plate.

U.S. Pat. No. 6,755,833 to Paul et al. shows a plate arrangement having circular holes and elongated slots extending in pairs along the length of the plate, and a flexible band that extends over the holes and slots to prevent backout of the screws after they are driven into bone. As with the Needham plate, screw translation is a function of the shapes and sizes of the holes and slots. Holes and slots with relatively short lengths serve as support apertures to fix the plate to one or more vertebrae. Slots with greater lengths allow the plate to translate at other levels. Starting at one end of the plate and moving to the other end, the length of each slot gets progressively longer, allowing more and more settlement as the slots get longer.

U.S. Pub. No. 2005/0049595 discloses a number of plates with different combinations of circular holes, elongated slots and carriage blocks. The circular holes rigidly fix the plate to an underlying vertebral body, and prevent screw translation relative to the plate at those hole locations. The slots and carriage blocks provide limited translation of screws relative to the plate. Settlement of vertebrae is limited to the specific arrangement of circular holes, slots and carriage blocks. The degree of translation provided by the carriage blocks is controlled by stop surfaces at specific locations on the plate. The amount of translation may be adjusted by using interchangeable carriage blocks of different shapes and styles.

One of the drawbacks of known plating systems is that the predefined hole and slot configurations dictate how settlement will occur, leaving the surgeon very few options for controlling the settlement of vertebrae prior to bony fusion (arthrodesis). Controlling where settlement occurs, and the manner in which settlement occurs, is important because settlement of one segment can seriously impact the function and condition of adjacent segments. In many fusion procedures, the patient has an adjacent disc that does not require surgery, but shows early signs of a degenerative condition. In such cases, it is desirable to prevent the segment adjacent the degenerating disc from settling or subsiding. Any vertebral motion adjacent the degenerating disc can change the spacing around the degenerating disc, which can aggravate the disc, limit its functionality, and accelerate degeneration of the disc. Holes and slots that dictate how settling occurs may not be designed to control settlement where that control is needed.

To avoid impacting adjacent discs, some surgeons choose plates with circular screw holes that rigidly fix the plate and screws, and prevent screw translation and settlement. This has its own set of potential problems. If the screws cannot translate in the plate, and the plate does not allow settlement, the fused segments will be stress-shielded by the screws and plate. The graft material will not be maintained under constant load, limiting bone growth and fusion in the stress-shielded segments.

A related drawback to known plating systems is that many plates limit settlement and screw translation to one direction, toward one end of the plate. For example, a number of plates feature circular holes at one end of the plate and slots arranged along the rest of the plate. The circular holes at the one end of the plate allow no screw translation, fixing the plate to the vertebra at that end. The slots allow their respective screws to translate, permitting settling to occur away from the fixed end. The slots offer no control over settlement at specific levels, however. Therefore, if a surgeon wants to allow settlement to occur at levels located away from the fixed end, but wants to vary the amount of settlement at different segments, the slots provide no control mechanism to do this.

Because slot configurations dictate how and where screw translation occurs, a surgeon may be compelled to carry an assortment of different plates, with each plate kept on hand to address a specific indication. For example, the surgeon may have to obtain a plate with circular holes at a center section or sections of the plate, and elongated slots or carriage blocks at the ends of the plate, to fix the screws at the center section or sections of the plate. For fusion procedures involving three-level plates having four rows of screws, the surgeon may need a plate with circular holes in the two interior rows to fix the plate at those sections, or a plate with circular holes at only one of the interior rows to fix the plate at that section only. Given so many plate options, the process of determining the proper plate to use can be difficult, particularly in procedures involving three or more levels. The surgeon must select a plate having the right combination of holes and slots, and the right selection of slot sizes and shapes, to control settlement in a desired manner.

In summary, systems that control screw translation as a function of slot geometry, carriage blocks and/or stop surfaces provide limited options for surgeons, and may compel hospitals to supply a large number of different fixation plates to give surgeons the options they need to address different contingencies.

SUMMARY

The drawbacks of known fixation plating systems are resolved to a large degree by Applicants' plating systems.

In one embodiment, the system includes an elongated plate having a first end, a second end and a longitudinal axis extending from the first end to the second end. The first end includes a first elongated slot having a long axis parallel to the longitudinal axis of the plate and a short axis perpendicular to the longitudinal axis of the plate. The second end includes a second elongated slot having a long axis parallel to the longitudinal axis of the plate and a short axis perpendicular to the longitudinal axis of the plate. The first and second elongated slots each have a seat portion. A first fastener includes a head and a shank, the shank having a diameter that is less than the lengths of the short axes of the first and second elongated slots so that the shank of the first fastener can be inserted through the first or second elongated slot. The head of the first fastener has a head profile configured to engage the seat portions of the first and second elongated slots in an interference fit to inhibit translation of the head within the first and second elongated slots. A second fastener has a head and a shank, the shank having a diameter that is also less than the lengths of the short axes of the first and second elongated slots so that the shank can be inserted through the first or second elongated slot. The head of the second fastener has a head profile configured to engage the seat portions of the first and second elongated slots in sliding engagement to allow translation of the head in the slots. The first fastener is selectively insertable into the first or second elongated slot in an interference fit to attach the plate to a first vertebra and restrict motion of the first vertebra relative to the plate. The second fastener is selectively insertable into the first or second elongated slot in a non-interference fit to attach the plate to a second vertebra and allow movement of the second vertebra relative to the plate.

Another embodiment includes an elongated plate having a first end, a second end and a longitudinal axis extending from the first end to the second end. The first end includes a first elongated slot having a long axis parallel to the longitudinal axis of the plate and a short axis perpendicular to the longitudinal axis of the plate. The second end includes a second elongated slot having a long axis parallel to the longitudinal axis of the plate and a short axis perpendicular to the longitudinal axis of the plate. The first and second elongated slots each have a seat portion. A first fastener includes a head and a shank, the shank of the first fastener being received through the first elongated slot and the head of the first fastener positioned in the seat portion of the first elongated slot in an interference fit to inhibit translation of the head within the first elongated slot. The second fastener has a head and a shank, the shank of the second fastener being received through the second elongated slot and the head of the second fastener positioned in the seat portion of the second elongated slot in a non-interference combination or assembly to allow translation of the head within the second elongated slot.

Another embodiment features a method of controlling the settling of vertebrae during fusion of a spine. One method includes the steps of placing a fixation plate over a first, second and third vertebrae, the fixation plate comprising a first end, a second end opposite the first end, and a midsection between the first and second ends, the fixation plate having elongated slots at the first end, second end and midsection, the elongated slots having identical configurations, positioning the fixation plate relative to the first, second and third vertebrae so that one of the longitudinal slots is aligned over each of said first, second and third vertebrae, selecting one of the first, second and third segments as a segment where settling is to be limited, inserting a semi-constrained fastener through an elongated slot that is adjacent the segment where settling is to be limited, anchoring the semi-constrained fastener into one of the first, second and third vertebrae, the semi-constrained fastener received in the plate in an interference fit, inserting dynamic fasteners through the remaining slots that do not receive the semi-constrained fastener, and anchoring the dynamic fasteners in the vertebrae, the dynamic fasteners having identical configurations and being received in the plate in a sliding arrangement to permit translation of the dynamic fasteners relative to the plate.

Another embodiment features a self-locking bone screw for attaching an implant to bone. The bone screw includes a screw body having a head and an elongated shank extending from the head. The head has a plurality of radially expandable petals that surround a hollow passage into the head. The passage includes a recess extending between the petals and a socket that extends from the recess into the shank. The recess includes a mouth section that forms an entrance into the passage from outside the head, a chamber having a seat section, and a lip between the mouth section and chamber, the lip projecting radially inwardly into the passage. The recess contains a spring having a ring shaped body portion and at least one deformable extension extending from the body portion. The body portion includes a smaller diameter section, a larger diameter section, and a shoulder between the smaller and larger diameter sections. The deformable extension engages the seat section in the chamber and creates a spring bias that holds the shoulder in abutment with the lip. The spring is moveable in the recess between a first operative position, in which the shoulder on the spring abuts the lip in the passage to expand the petals radially outwardly and lock them in the radially expanded position, and a second operative position, in which the shoulder is displaced out of abutment with the lip to unlock the petals and allow them to retract radially inwardly.

BRIEF DESCRIPTION OF THE DRAWINGS

The embodiments that will be described will be better understood in conjunction with the drawing figures, of which.

DETAILED DESCRIPTION

Although the following description is provided with reference to specific embodiments, the description is not intended to be limited to the details shown and described. Various modifications may be made in the details within the scope and range of equivalents of the claims.

Applicants' cervical plating systems can be configured and adjusted in numerous ways to control how settling occurs at fusion segments. The plating systems allow settling to be controlled at each individual segment. More specifically, the plating systems allow translation of bone screws to be controlled during postoperative settling. The plating system controls not only the amount of screw translation but also the direction of translation of each screw relative to the plate, and each screw's relative resistance to translation. This allows the surgeon to control the amount of compression and stress shielding at each segment. The amount of settling and direction of settling at each segment is not a function of the hole or slot configuration, but rather a function of screw head geometry that is selected for a particular slot. As a result, all of the slots in the plate can be identically configured, and a surgeon can use one plate design in multiple possible settings to control translation and settling, without worrying about the hole and slot configurations. By making screw translation a function of screw head configuration, one plate configuration can provide numerous options for controlling settling.

As noted above, many known plating systems limit screw translation by limiting the length of the slots. Screws that are to be fixed against translation are placed in circular holes. In contrast to these systems, Applicants' plating systems limit screw translation by providing different screw head options that differ in terms of how much translation they allow. Applicants' plates contain slots that leave it to the surgeon to decide whether screw translation is to be permitted at each level, to what extent translation occurs, the relative resistance to translation and the direction of translation. In a preferred embodiment, the plating system features a plate with elongated slots only, and two types of screws. The first type of screw has a "semi-constrained" screw head configuration, and the second type of screw has a "dynamic" screw head configuration. The term "semi-constrained", as the term is used in reference to screws, is defined herein as a screw head configuration that allows the screw head to pivot polyaxially in a slot, but substantially prevents the screw head from translating in the slot without an increase in resistance. This is preferably established by an interference fit between the screw head and a seat portion in the slot. The term "dynamic", as the term is used in reference to screw heads, is defined herein as a screw head configuration that allows the screw head to both pivot polyaxially in a slot and freely translate in the slot.

The semi-constrained screws and dynamic screws can be used in combination in one plate to provide rigid fixation at one section of the plate, and allow vertebral motion at other sections of the plate. This combination of rigid fixation and settlement in one plate may be referred to as "semi-dynamic". In a semi-dynamic plate assembly, the semi-constrained screws exhibit "resistive translation", a condition in which the heads of the screws can pivot but cannot translate freely in their respective slots. The dynamic screws can both pivot and translate freely in their respective slots, absorbing the natural anatomical physical settling with the system. As a result, vertebrae that hold dynamic screws can move relative to the plate during settlement.

In one embodiment, a fixation plate system includes:

an elongated plate having a first end, a second end and a longitudinal axis extending from the first end to the second end, the first end comprising a first elongated slot having a long axis parallel to the longitudinal axis of the plate and a short axis perpendicular to the longitudinal axis of the plate, the second end comprising a second elongated slot having a long axis parallel to the longitudinal axis of the plate and a short axis perpendicular to the longitudinal axis of the plate, the first and second elongated slots each having a seat portion;

a first fastener having a head and a shank, the shank of the first fastener having a diameter that is less than the lengths of the short axes of the first and second elongated slots so that the shank of the first fastener is configured for insertion through the first and second elongated slots, the head of the first fastener having a head profile configured to engage the seat portions of the first and second elongated slots in an interference fit to inhibit translation of the head within the first and second elongated slots; and a second fastener having a head and a shank, the shank of the second fastener having a diameter that is less than the lengths of the short axes of the first and second elongated slots so that the shank of the second fastener is configured for insertion through the first and second elongated slots, the head of the second fastener having a head profile configured to engage the seat portions of the first and second elongated slots in sliding engagement to allow translation of the head within the first and second elongated slots, the first fastener selectively insertable into the first or second elongated slot in an interference fit to attach the plate to a first vertebra and restrict motion of the first vertebra relative to the plate, the second fastener selectively insertable into the first or second elongated slot in a non-interference fit to attach the plate to a second vertebra and allow translation of the second vertebra relative to the plate.

In another embodiment, a fixation plate system includes:

an elongated plate having a first end, a second end and a longitudinal axis extending from the first end to the second end, the first end comprising a first elongated slot having a long axis parallel to the longitudinal axis of the plate and a short axis perpendicular to the longitudinal axis of the plate, the second end comprising a second elongated slot having a long axis parallel to the longitudinal axis of the plate and a short axis perpendicular to the longitudinal axis of the plate, the first and second elongated slots each having a seat portion;

a first fastener having a head and a shank, the shank of the first fastener extending through the first elongated slot and the head of the first fastener positioned in the seat portion of the first elongated slot in an interference fit to inhibit translation of the head within the first elongated slot; and a second fastener having a head and a shank, the shank of the second fastener extending through the second elongated slot and the head of the second fastener positioned in the seat portion of the second elongated slot in a non-interference fit to allow translation of the head within the second elongated slot.

Applicants' plate assemblies may be used in one or more types of procedures. In one method, a surgeon uses the plate assembly by:

placing a fixation plate over first, second and third vertebrae, the fixation plate comprising a first end, a second end opposite the first end, and a midsection between the first and second ends, the fixation plate having elongated slots at the first end, second end and midsection, the elongated slots having identical configurations;

positioning the fixation plate relative to the first, second and third vertebrae so that one of the longitudinal slots is aligned over each of said first, second and third vertebrae;

selecting one of the first, second and third segments as a segment where settling is to be limited;

inserting a semi-constrained fastener through one of the elongated slots that is adjacent the segment where settling is to be limited;

anchoring the semi-constrained fastener into one of said first, second and third vertebrae, the semi-constrained fastener received in the plate in an interference fit; and inserting dynamic fasteners through the elongated slots that do not receive the semi-constrained fastener and anchoring the dynamic fasteners in the vertebrae that do not receive the semi-constrained fastener, the dynamic fasteners extending through the plate in a sliding arrangement to permit translation of the dynamic fasteners relative to the plate, wherein during fusion of the first vertebra and second vertebra, and fusion of the second vertebra and third vertebra, the semi-constrained fastener remains fixed relative to the plate in its respective slot, and the dynamic fasteners translate relative to the plate in their respective slots toward the semi-constrained fastener to facilitate settlement motion toward the location of the semi-constrained fastener.

To customize the amount of fixation and settlement, Applicants' plate assemblies utilize self-locking screws, which may include:

a screw body having a head and an elongated shank extending from the head a plurality of radially expandable petals on the head a passage extending through the head and into the shank, the passage having a recess extending between the petals and a socket that extends from the recess into the shank, the recess comprising a mouth section that forms an entrance into the passage from outside the head, and a chamber having a seat section, the mouth section having a first diameter, the chamber having a second diameter larger than the first diameter of the mouth section so as to form a lip between the mouth section and chamber, the lip projecting radially inwardly into the passage; and a spring having a ring shaped body portion and at least one deformable extension extending from the body portion, the body portion comprising a smaller diameter section, a larger diameter section, and a shoulder between the smaller and larger diameter sections, the at least one deformable extension engaging the seat section in the chamber and creating a spring bias that holds the shoulder in abutment with the lip to expand the petals radially outwardly and lock them in the radially expanded position.

Figure 1:
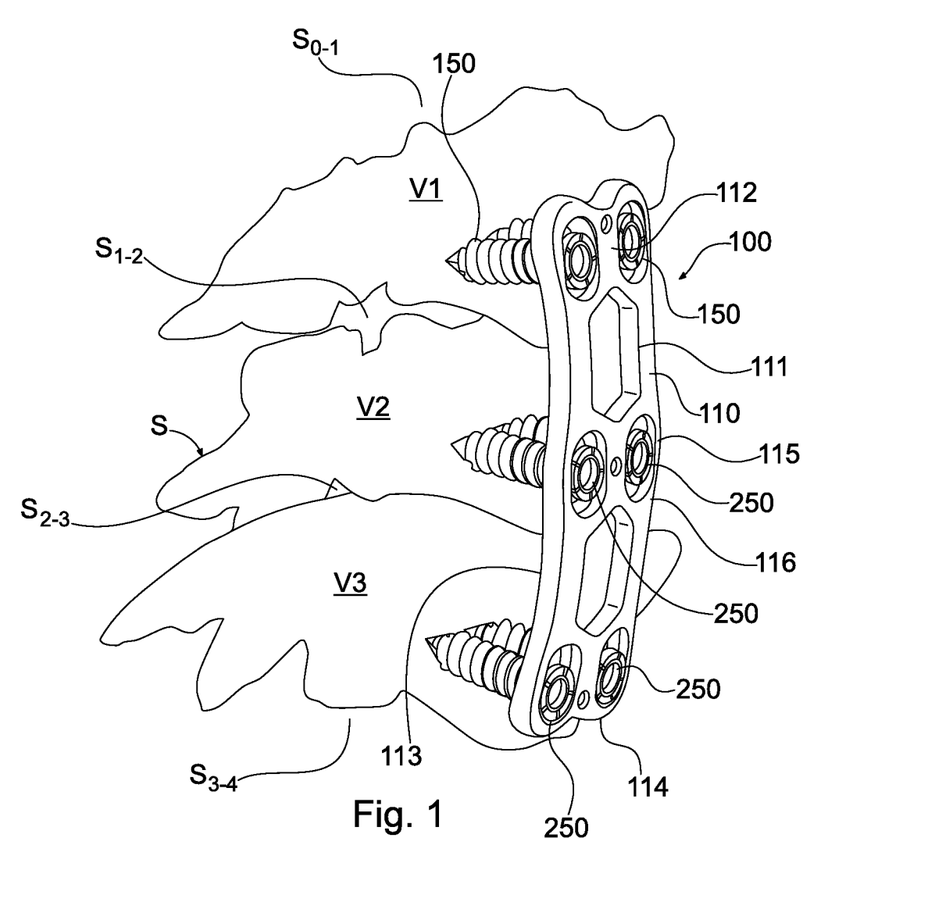
FIG. 1 is a perspective view of a plating system in accordance with one embodiment, schematically shown on a human spine as the system would appear in one possible arrangement.

Applicants' cervical plating systems may be used in single-level fusion procedures, or multiple-level fusion procedures. Referring now to FIG. 1, a cervical plating system 100 is illustrated in a two-level fusion procedure. Although plating system 100 includes a plate with three rows of slots, it will be understood that plates in accordance with the invention may have only two rows of slots for a single level fusion procedure. Alternatively, plates in accordance with the invention may have four or more rows of slots for multiple-level procedures. Therefore, the embodiment illustrated in FIG. 1 is not intended to limit the type of plate used, the number of slot rows in the plate, or the number of levels that can be fused in accordance with embodiments of the invention.

Plating system 100 is shown implanted in three vertebrae, V1, V2 and V3 of a spinal column S. Spinal column S is only partially shown for clarity. Four spinal segments, $S_{0-1}$, $S_{1-2}$, $S_{2-3}$ and $S_{3-4}$ are also shown. System 100 includes a plate 110 that is secured to spinal column S with a plurality of fasteners or anchor elements that will be described below in greater detail. Plate 110 has a first end 112, a second end 114 and a mid section 116 extending from the first end to the second end. In addition, plate 110 has a front face 111 and a rear face 113 opposite the front face. Plate 110 follows a slight bend 115, wherein midsection 116 projects in the direction of front face 111 as shown.

Figure 2:
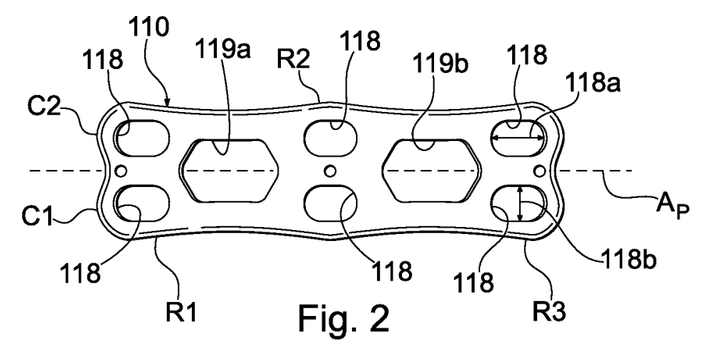
FIG. 2 is a top view of a plate used in the system shown in FIG. 1.

Referring to FIG. 2, plate 110 features six elongated slots 118 that are arranged in pairs and divided into three rows as shown. Each slot 118 is adapted to receive an anchor element to secure the plate to spinal column S. A first row R1 of slots 118 is positioned at first end 112, a second row R2 of slots is positioned at midsection 116, and a third row R3 of slots is positioned at second end 114. First, second and third rows R1, R2 and R3 are arranged so as to form a first column C1 of slots and a second column C2 of slots. Each slot has a long axis 118a and a short axis 118b. The long axes 118a in second row R2 are slightly larger than the long axes in first row R1 and third row R3. In one example, the long axes in second row R2 each measure 3.0 mm, and the long axes in the first and third rows R1 and R3 each measure 2.5 mm. The short axes 118b in first, second and third rows R1, R2 and R3 are the same length. Because of bend 115, the orientations of slots 118 varies from row to row. Each pair of slots within a row shares the same planar orientation, but that planar orientation differs from the planar orientations of the slots in the other two rows due to the curvature of plate 110.

Plate 110 includes a first aperture 119a and a second aperture 119b. Apertures 119a and 119b are designed to allow graft material to be viewed or observed through the plate in the disc space during a fusion procedure. First aperture 119a extends between first row R1 and second row R2, and between first column C1 and second column C2. Second aperture 119b extends between second row R2 and third row R3, and between first column C1 and second column C2. First and second apertures 119a and 119b are centered along the longitudinal axis $A_P$ of plate 110.

Referring again to FIG. 1, plate 110 is secured to vertebrae V1, V2 and V3 by bone screws that are driven through slots 118. Plating system 100 includes two semi-constrained screws 150 and four dynamic screws 250. As defined previously, semi-constrained screws 150 have a screw head configuration that allows the screw head to pivot polyaxially in a slot, but substantially prevents the screw head from translating in the slots 118. Dynamic screws 250, in contrast, have a screw head configuration that allows both polyaxial motion and unrestricted translation in the slots 118. Semi-constrained screws 150 and dynamic screws 250 may be formed of variety of biocompatible materials. A preferred material is Titanium alloy, such as Ti6A14 V.

Figure 3:
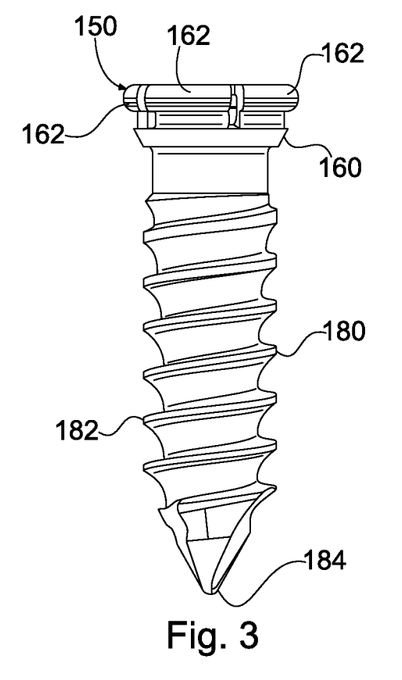
FIG. 3 is a side view of a screw used in the system shown in FIG. 1.
Figure 4:
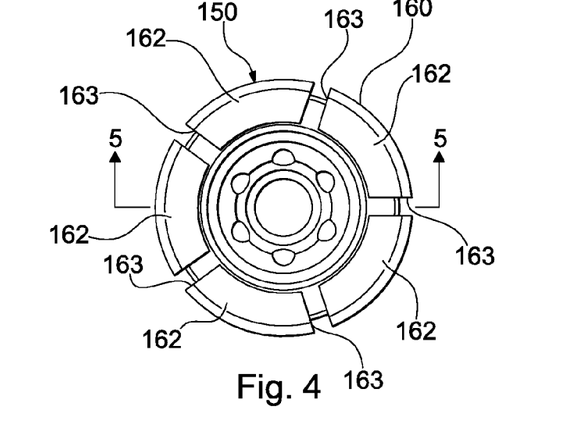
FIG. 4 is a top view of the screw shown in FIG. 3.
Figure 5:
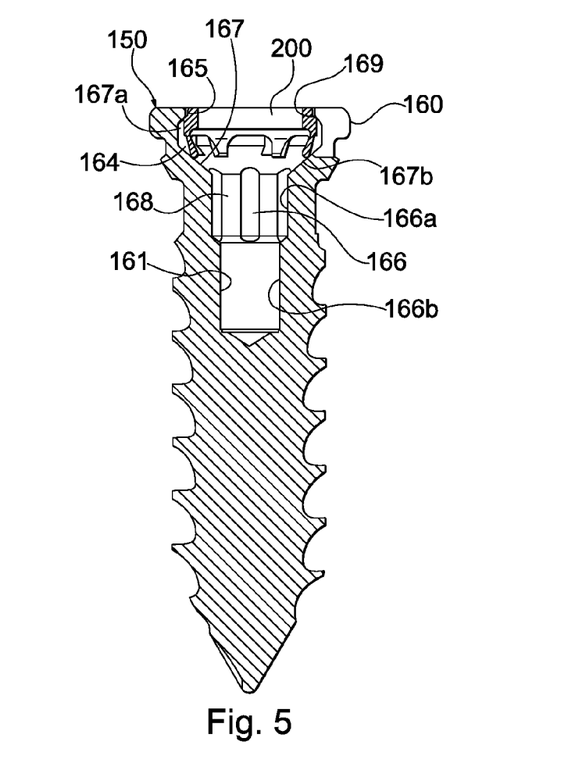
FIG. 5 is a side cross-section view of the screw shown in FIG. 3.

Referring to FIGS. 3-5, a semi-constrained screw 150 will be described. Semi-constrained screws 150 have virtually identical head and spherical seat configurations as dynamic screws, but semi-constrained screws have slightly larger head dimensions. The shank portions of the semi-constrained screws 150 and dynamic screws 250 are identical. Therefore, semi-constrained screw 150 will be described with the understanding that the elements on the semi-constrained screw head are present on the dynamic screw head, but differ in terms of size.

Semi-constrained screw 150 includes a head 160 and an elongated shank 180 that extends from the head. Shank 180 has an external thread 182 and a stabbing, non-deformable tip 184. Head 160 is similar in many respects to the screw head shown in Applicant's U.S. application Ser. No. 11/732,752 (U.S. Pub. No. 2007/0288025), the contents of which is incorporated by reference herein in its entirety and for all purposes. Head 160 has a plurality of radially expandable and elastically deformable petals 162 that surround a hollow passage 161 that extends through the head and into the shank. Passage 161 includes a recess 164 between petals 162. Petals 162 are separated from one another by small gaps 163 that allow the petals to be expanded or wedged apart in a radially outward direction, and retracted or compressed back in a radially inward direction. Passage 161 also includes a socket 166 that extends from recess 164 into the interior of shank 180. Socket 166 features a first section 166a with an engagement surface 168, and a second section 166b. Engagement surface 168 has a removal thread configured to mate with the tip of a modified hexalobular driver for inserting and removing screw 150. It will be appreciated that a number of different engagement surfaces may be used in socket 166, including but not limited to a hexagonal socket configuration.

Recess 164 has a circular mouth section 165 that serves as an entrance into the recess and socket 166. Recess 164 also has a chamber 167 extending between the mouth section 165 and socket 166. Chamber 167 has a straight wall section 167a and a tapered seat section 167b. Mouth section 165 has a smaller diameter than straight wall section 167a of recess 164, forming a constriction or lip 169.

Petals 162 are resiliently flexible and biased radially outwardly into an expanded state by an elastically deformable spring 200 that is held captive in recess 164. Spring 200 may be formed of variety of biocompatible materials. A preferred material is Phynox, a Cobalt-Chromium-Nickel alloy which provides high strength, ductility and good mechanical properties. Phynox also has excellent fatigue life, corrosion resistance and is non-magnetic.

Figure 6:
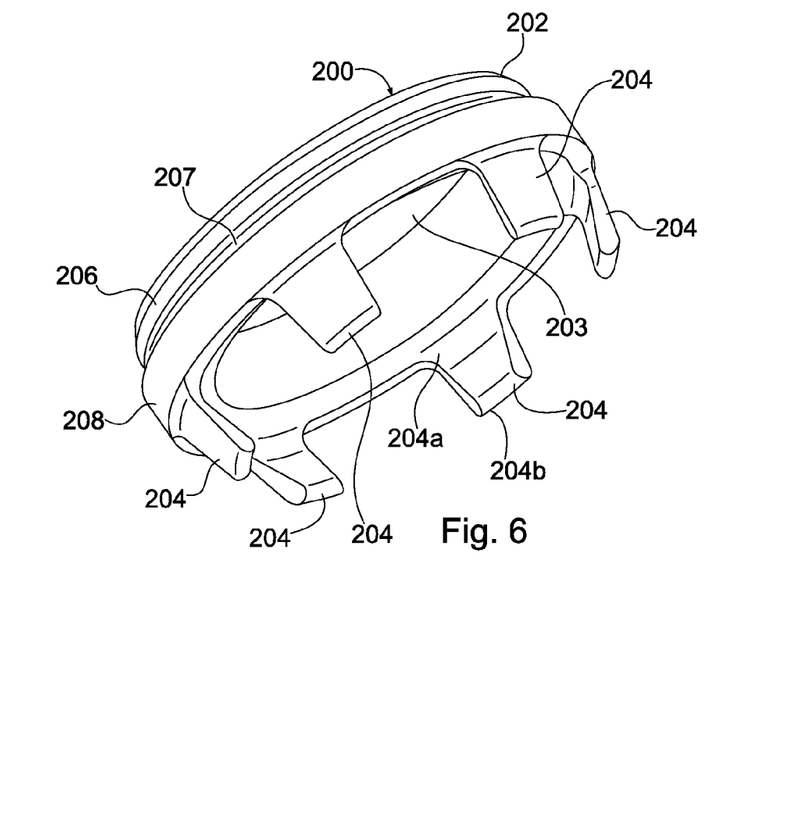
FIG. 6 is a perspective view of a spring component used in the screw shown in FIG. 3.
Figure 7:
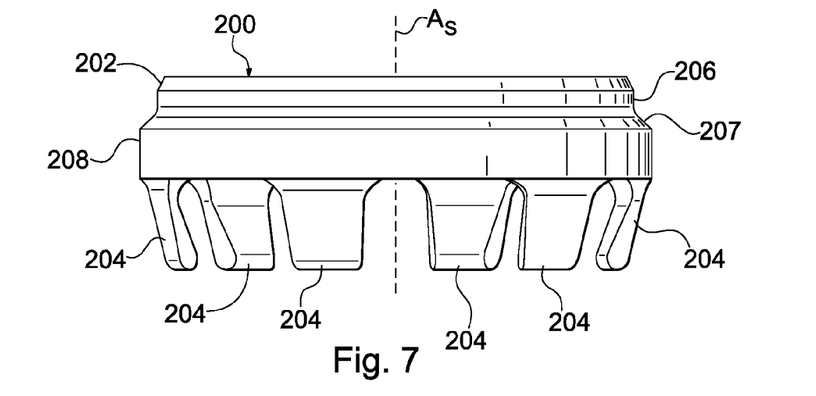
FIG. 7 is a side view of the spring component shown in FIG. 6.

Referring to FIGS. 6 and 7, spring 200 has ring shaped body portion 202 and six deformable legs 204 extending from the body portion. Legs 204 are arranged in a circular array and evenly spaced from one another relative to the circumference of body portion 202. Body portion 202 surrounds a central opening 203 that aligns substantially coaxially with socket 166 when the spring is positioned in recess 164. Central opening 203 permits insertion of an instrument, such as a driver, through spring 200 and into socket 166. Body portion 202 has a smaller diameter section 206 and a larger diameter section 208, creating a shoulder 207 between the smaller and larger diameter sections. Legs 204 extend in a circular arrangement and project radially inwardly with respect to a central longitudinal axis $A_S$ of spring 200. Each leg 204 has a first end 204a that connects the leg to body portion 202 and a second end 204b that remains free. The width of each leg 204 is wider at first end 204a than at second end 204b, with each leg gradually tapering from the first end to the second end.

Although spring 200 is shown with a closed circular body portion 202 and a plurality of legs 204, a number of other spring designs may be used. For example, the spring need not have a closed ring-shaped body, and may instead be open or split, like a C-shaped ring. A closed ring structure provides a uniform bias force, both axially and radially, and maintains the spring in a centered position in the passage. Therefore, the closed structure may work better than open structures, although open structures may be suitable. The spring also need not have six legs as shown, but may instead have fewer or more legs. For example, the spring may have a single annular flange with a slit at one or more sections that allow the flange to flex inwardly or outwardly.

Figure 8:
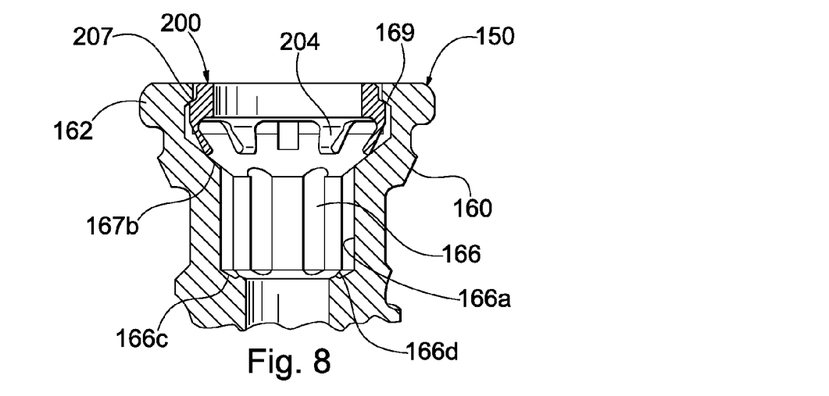
FIG. 8 is a truncated side cross-section view of the screw shown in FIG. 3, showing an interior component in a first condition.
Figure 9:
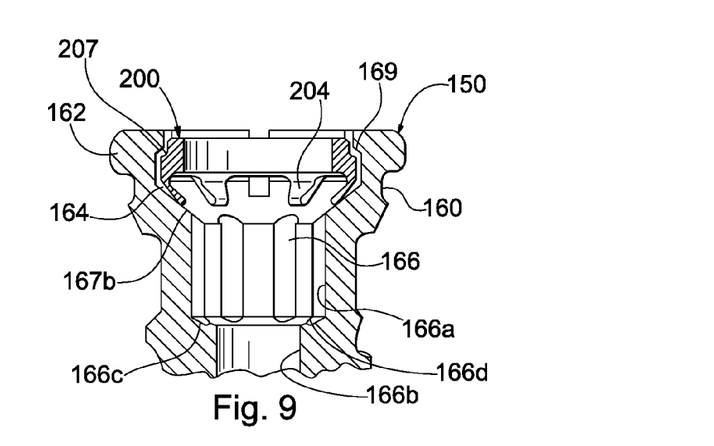
FIG. 9 is a truncated side cross-section view of the screw shown in FIG. 3, showing an interior component in a second condition.
Figure 10:
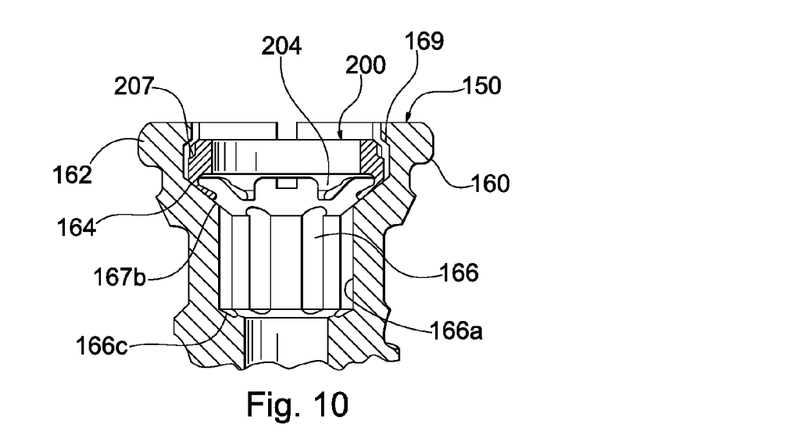
FIG. 10 is a truncated side cross-section view of the screw shown in FIG. 3, showing an interior component in a third condition.

Spring 200 is movable in recess 164 to three different operative positions shown in FIGS. 8-10. Specifically, spring 200 is operable in a first position shown in FIG. 8, in which shoulder 207 abuts against lip 169. In this state, spring 200 exerts axial and radial force against petals 162, spreading them radially outwardly to an expanded condition in which the diameter of the screw head is enlarged. Spring 200 is biased toward this first position by legs 204, which push up from seat section 167b. In this arrangement, spring 200 expands the size of the screw head to secure the head in a hole or slot.

Spring 200 is movable to a second operative position shown in FIG. 9 to release the screw from inside a hole or slot. Because spring 200 is maintained in the first position by the biasing force provided by legs 204, the biasing force must be overcome before the screw can be moved to the second position. A surgical driver or other instrument can be inserted into recess 164 and socket 166 to push spring 200 downwardly against the biasing force of legs 204 and into the second position. In the second position, spring 200 is displaced distally in the recess toward socket 166, so that shoulder 207 is separated from lip 169. Because shoulder 207 no longer engages lip 169, petals 162 are released and free to move radially inwardly to disengage the screw head from the hole or slot. Legs 204 are compressed against seat section 167b and bend radially inwardly as shown. In this state, legs 204 are elastically deformed with stored energy. The elastic property of legs 204 provides a first safety mechanism that prevents damage to the spring in the event the instrument is overdriven through spring 200.

Upon removal of the surgical driver or other tool, the stored energy in legs 204 is released to return the legs to their relaxed state. As legs 204 return to their relaxed state, the legs once again push up from seat section 167b and move shoulder 207 back into engagement with lip 169 in the first position. Petals 162 are once again forced outwardly by the radial and axial force exerted by spring 200. The engagement between lip 169 and shoulder 207 prevents spring 200 from exiting the recess, so that the spring remains captive in screw head 160.

Screw drivers used with Applicants' assemblies preferably include a bit that bottoms out at a bottom surface 166c in first section 166a of socket 166. Bottom surface 166a forms a positive stop 166d that limits how far the driver can advance, which in turn limits how far spring 200 is advanced by the driver in recess 164. Stop 166*d* prevents the driver from advancing spring 200 past the second operative position in FIG. 9. This provides a second safety mechanism to prevent damage to the spring. In particular, the stop 166*d* limits how far the spring is advanced, and consequently, how much the legs are compressed. As will be explained next, spring 200 can still be advanced past the second operative position using other instruments that do not bottom out at surface 166*a*.

Referring to FIG. 10, spring 200 is shown displaced past the second operative position into a third position in recess 164. Spring 200 can only be advanced to the third position with a special removal tool. In the third position, shoulder 207 is moved even further away from lip 169. Legs 204 are compressed further against seat section 167*b* and bend further inwardly. The stress on each leg 204 exceeds the elastic limit, so that the legs undergo plastic deformation and irreversible shape change. At this stage, the spring is no longer capable of returning to the first position to expand petals 162 and secure the screw head in a screw hole. Spring 200 is permanently damaged so that the screw cannot be reused.

Spring 200 remains captive in mouth section 165 and chamber 167, and cannot enter socket 166. Spring 200 is operable to expand or release petals 162 but cannot obstruct or interfere with socket 166. That is, a driver can be inserted through spring 200 and into the socket 166 without being obstructed by the spring. Ring shaped body portion 202 provides a friction coupling that allows drivers and other tools to engage the screw in a "stab fit" and remain coupled to the screw so the screw does not slip off the driver tip. The driver tip can be inserted into the screw head and through spring 200 in a stabbing motion, at which point the interior of ring shaped body 202 frictionally engages the driver to hold the spring on the driver tip. Because spring 200 does not extend into socket 166, the driver tip can mate directly with the interior wall of the screw. This is a significant advantage, because a direct engagement between the driver tip and interior wall of the screw provides tactile feel that helps the surgeon determine when the screw is fully tightened or loose.

Semi-constrained screw 150 and dynamic screw 250 each incorporate spring 200. As noted above, spring 200 is operable to expand petals 162 in the screw heads to restrict movement of the screw heads in slots 118. Semi-constrained screw 150 and dynamic screw 250 have different screw head dimensions and geometries. Because of these differences, the two screws behave differently when seated in the same slot configuration. The semi-constrained screw head, which is slightly larger than the dynamic screw head, can pivot in the slot, allowing polyaxial movement, but is substantially prevented from translating in the slot. In this arrangement, the semi-constrained screw allows for "rotational settling". That is, when a vertebral body settles, the bone screw attached to that vertebral body pivots with respect to the plate. During this pivot motion, the screw head remains in one location in the slot and does not translate along the length of the slot. The dynamic screw head is slightly smaller than the semi-constrained screw head and is not held by an interference fit. As a result, the dynamic screw head allows the screw to both pivot in a polyaxial range of motion, and translate in the slot. In this arrangement, the dynamic screw allows for "translational and rotational settling". That is, when a vertebral body settles, the bone screw attached to that vertebral body pivots and translates with respect to the plate.

Figure 11:
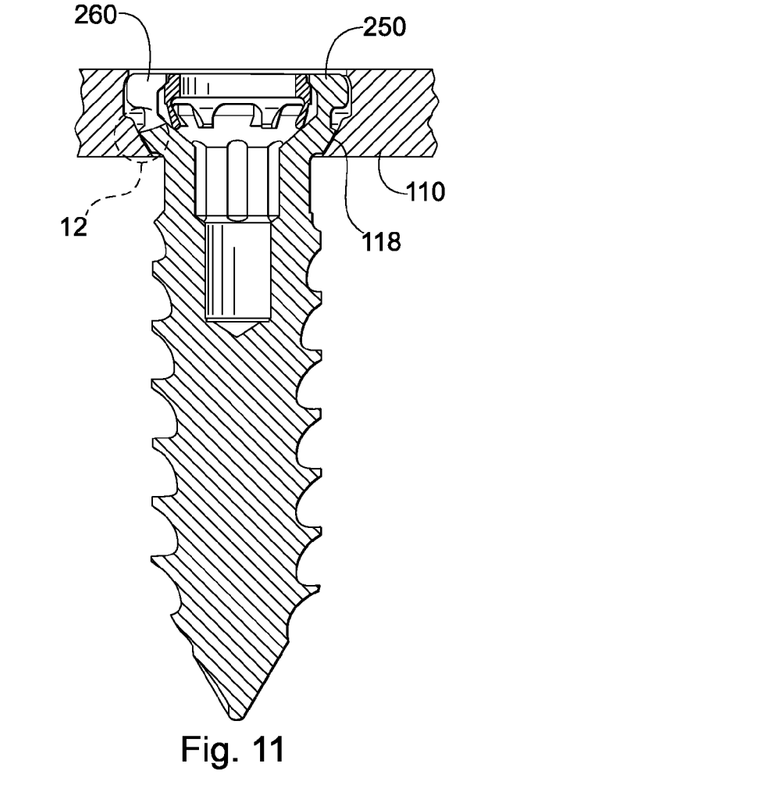
FIG. 11 is a truncated side cross-sectional view of the plate used in the system shown in FIG. 1, with a first screw inserted through the plate.
Figure 12:
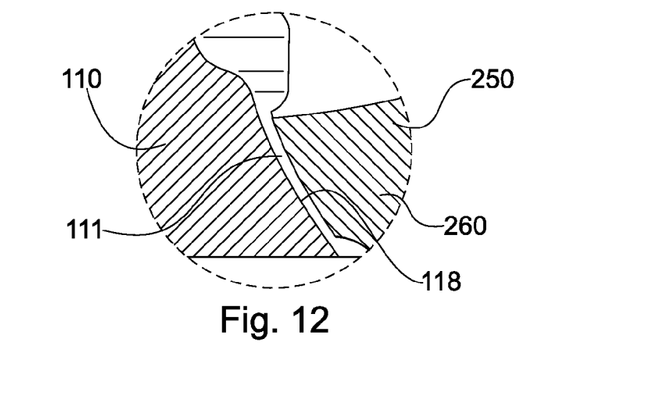
FIG. 12 is an enlarged view of one portion of FIG. 11.

FIGS. 11 and 12 show a dynamic screw 250 in plate 110. As can be seen, dynamic screw 250 has a head 260 with dimensions that provide a small amount of clearance space 111 between the head and the seat of slot 118. As such, head 260 can pivot in slot 118 and translate freely in the slot.

Figure 13:
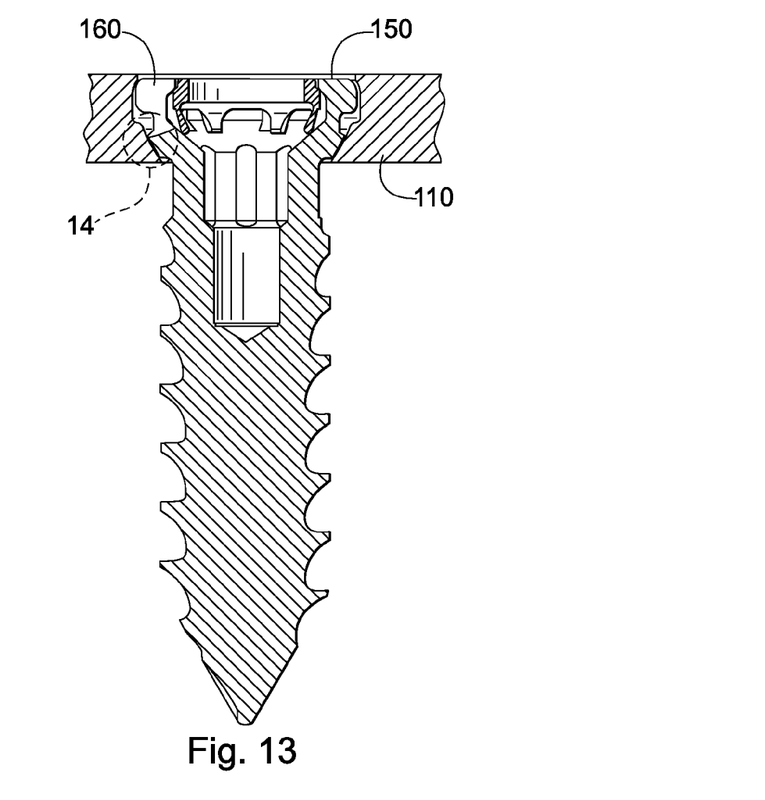
FIG. 13 is a truncated side cross-sectional view of the plate used in the system shown in FIG. 1, with a second screw inserted through the plate.
Figure 14:
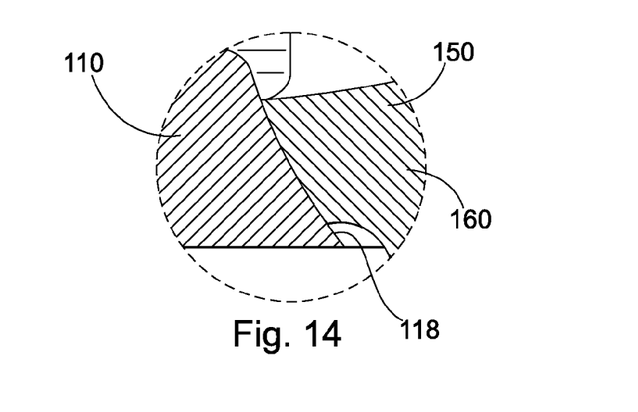
FIG. 14 is an enlarged view of one portion of FIG. 13.

FIGS. 13 and 14 show a semi-constrained screw 150 in plate 110. As can be seen, semi-constrained screw 150 has a head 160 with larger dimensions than screw head 260. As such, screw head 160 engages slot 118 in an interference fit. Head 160 can pivot in place in slot 118, but translation is substantially prevented.

By offering two different screw configurations 150 and 250 and one slot configuration 118, plating system 100 provides an intraoperative, fully customizable fixation system. Plating system 100 offers the surgeon multiple fixation rigidity options with the ability to vary rigidity fixation within a single plate. That is, the settlement of each vertebra can be controlled and customized at each segment in a single plate construct, without concern for having a particular hole and slot arrangement. Depending on which screw is used, a different and unique locking mechanism is applied at each segment to control settlement. A unique locking mechanism may be configured at any one level of a multiple-level fusion plate. Choosing the semi-constrained screw 150 allows for rotational settling of the screw in slot 118, while choosing the dynamic screw 250 allows for both translational and rotational settling in the slot. This affords the surgeon multiple possibilities with regard to both the type and location of settling that occurs after surgery. This benefit becomes particularly advantageous in multi-level reconstructions. Applicants' systems may be applied to the cervical, thoracic or lumbar spine.

One of the advantages of Applicants' plate assemblies is that damage to adjacent levels can be minimized or prevented without sacrificing the ability to customize the rigidity fixation at each level. As noted above, dynamic plates can pose a risk to adjacent degenerative discs. Known plate assemblies address this concern by providing circular holes at the end of the plate that will be placed next to the degenerative disc, so that the plate does not impinge on the degenerative disc. While this may protect the degenerative disc against settlement of the adjacent segment, it prevents the surgeon from fully controlling the amount of settlement at other segments, particularly those near the opposite end of the plate. Applicants's plate assemblies, in contrast to known plate assemblies, provide surgeons with options that can be tailored for individually specific case scenarios.

EXAMPLE

Figure 15:
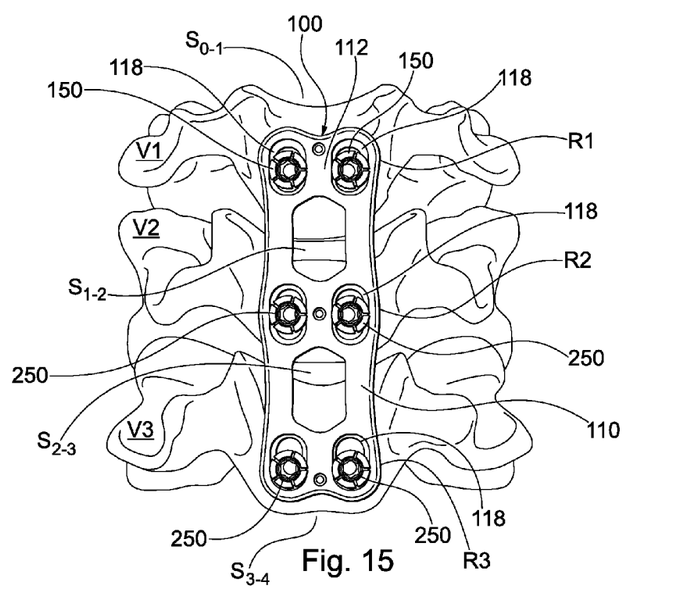
FIG. 15 is a front view of the plating system shown in FIG. 1, the plating system shown after a first passage of time after a fusion procedure.

Referring now to FIG. 15, the use of plate system 100 will be described in one example of a two-level fusion procedure involving three vertebrae, V1, V2 and V3. Four spinal segments, $S_{0-1}$, $S_{1-2}$, $S_{2-3}$ and $S_{3-4}$ are shown, with segments $S_{1-2}$ and $S_{2-3}$ being fused. Plate system 100 is shown in FIG. 15 as it would appear immediately after surgery, and prior to any settlement. Prior to surgery, the disc at segment $S_{0-1}$ is identified as having a degenerative condition in the early stages. Because segment $S_{0-1}$ is adjacent to the fusion site, it is preferable to limit or prevent relative movement of V1. Therefore, two semi-constrained screws 150 are selected and placed in slots 118 of first row R1 to attach plate 110 to vertebra V1. Semi-constrained screws 150 are driven into vertebra V1 and anchor the end of plate 110 in a position that remains fixed relative to vertebra V1. The screw heads on screws 150 engage slots 118 in an interference fit that allows the screw heads to pivot through polyaxial motion but not translate in the slots.

Although first end 112 of plate 110 is fixed at V1, plate assembly 100 still allows settlement to occur in a controlled manner at segments $S_{1-2}$ and $S_{2-3}$ to maintain constant loading on the fusion material. To allow for settlement at segments $S_{1-2}$ and $S_{2-3}$, dynamic screws 250 are inserted in slots 118 at second row R2 and third row R3. With this arrangement, vertebrae V2 and V3 are free to move toward V1 relative to plate 110 during settlement.

Figure 16:
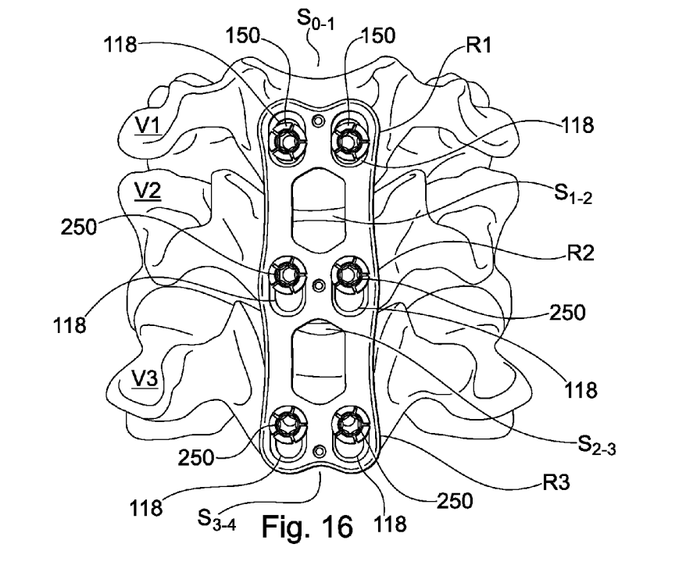
FIG. 16 is a front view of the plating system shown in FIG. 1, the plating system shown after a second passage of time after a fusion procedure.

FIG. 16 shows plate system 100 as it would appear after settlement is completed. As can be seen, semi-constrained screws 150 remain in the same position in the first row R1, while dynamic screws 250 have translated to a different position in second and third rows R2 and R3. In particular, dynamic screws 250 have moved in a cranial direction relative to plate 110, allowing V2 and V3 to also move in a cranial direction relative to V1. Accordingly, segments $S_{1-2}$ and $S_{2-3}$ are compressed while segment $S_{0-1}$ is not impacted. Had the first row R1 contained dynamic screws 250 like second and third rows R2 and R3, with the screws initially positioned as shown in FIG. 15, settlement would have occurred differently. All three pairs of screws would have translated relative to plate 110, with load being shared in segments $S_{1-2}$, $S_{2-3}$ and $S_{3-4}$.

The amount of movement of V2 and V3 relative to V1 can be controlled by controlling the amount of translation available to screws 250 in rows R2 and R3. The amount of translation available to each screw 250 can be controlled based on the initial position of each screw 250 in each slot 118. Referring back to FIG. 15, dynamic screws 250 are placed in the middle of slots 118 in row R2, and placed at the caudal ends of slots 118 in row R3. In this arrangement, dynamic screws 250 in row R3 can translate farther relative to the plate than the dynamic screws in row R2, because the screws in row R3 have more room to travel in slots 118 than the screws in row R2. Accordingly, more settlement is permitted to occur at segment $S_{2-3}$ than at $S_{1-2}$. The surgeon may opt to control the translation at each segment using the initial screw placement shown in FIG. 15, or a different arrangement, the results being based on which type of screw is selected for a particular row, and the relative position of dynamic screws in their respective slots. To allow for equal amounts of settlement at $S_{1-2}$ and $S_{2-3}$, for example, screws 250 can be placed at the same positions in each of the slots 118 in rows R2 and R3. Alternatively, screws 250 can be placed at the caudal ends of the slots 118 in row R2, and at the middle sections of the slots in row R3, to allow more screw translation in row R2.

While preferred embodiments have been shown and described herein, it will be understood that such embodiments are provided by way of example only. Numerous variations, changes and substitutions will occur to those skilled in the art without departing from the scope of this disclosure. For example, Applicants' assemblies need not be limited to two-level procedures, and may include plates designed for one level of fusion, or three or more levels of fusion. In such cases, the plates may have elongated slots of identical configurations, similar or identical to slots 118. For example, a plate may include a two rows of slots for a one level fusion. Such a plate may have a single row with a pair of dynamic screws (DY) and a single row with a pair of semi-constrained screws (SC). Alternatively, the plate may include six rows of slots for a five-level fusion. Any combination of screws may be used to achieve a desired effect in such a plate. For example, the plate may have alternating rows of semi-constrained screws (SC) and dynamic screws (DY) in the following order: SC-DY-SC-DY-SC-DY. Or the plate may include a single row with semi-constrained screws and the remaining rows having dynamic screws, in the following order: DY-SC-DY-DY-DY-DY. Moreover, the plate may include multiple dynamic screws concentrated together, and surrounded by dynamic screws, in the following arrangement, for example: SC-SC-DY-DY-SC-SC. Accordingly, components in accordance with the present invention may be used on single level or multiple level fusion procedures, with screws arranged in various configurations to control how settlement occurs. It is intended that the appended claims cover all such variations as fall within the scope of this disclosure.

What is claimed:

1. A fixation plate system comprising:
an elongated plate having a first end, a second end and a longitudinal axis extending from the first end to the second end, the first end comprising a first elongated slot having a long axis and a short axis, the second end comprising a second elongated slot having a long axis and a short axis, the first and second elongated slots each having a seat portion, the short axis of the first elongated slot equal in length to the short axis of the second elongated slot;
a semi-constrained fastener having a radially expandable head and a shank, the head of the semi-constrained fastener comprising a plurality of elastically deformable petals, the shank of the semi-constrained fastener having a diameter that is less than the lengths of the short axes of the first and second elongated slots so that the shank of the semi-constrained fastener is configured for insertion through the first and second elongated slots, the head of the semi-constrained fastener having a head profile with a diameter configured to engage the seat portions of the first and second elongated slots in an interference fit to inhibit translation of the head within the first and second elongated slots; and
a dynamic fastener having a radially expandable head and a shank, the head of the dynamic fastener comprising a plurality of elastically deformable petals, the shank of the dynamic fastener having a diameter that is less than the lengths of the short axes of the first and second elongated slots so that the shank of the dynamic fastener is configured for insertion through the first and second elongated slots, the head of the dynamic fastener having a head profile with a diameter configured to engage the seat portions of the first and second elongated slots in sliding engagement to allow translation of the head within the first and second elongated slots,
the diameter of the head of the semi-constrained fastener being greater than the diameter of the head of the dynamic fastener such that the semi-constrained fastener is selectively insertable into the first or second elongated slot in an interference fit to attach the plate to a first vertebra and restrict motion of the plate relative to the first vertebra, and
the dynamic fastener is selectively insertable into the first or second elongated slot in a non-interference fit to attach the plate to a second vertebra and allow translation of the plate relative to the second vertebra.

2. The fixation plate system of claim 1, wherein the first elongated slot at the first end of the plate comprises a pair of elongated slots.

3. The fixation plate system of claim 1, wherein the second elongated slot at the second end of the plate comprises a pair of elongated slots.

4. The fixation plate system of claim 1, wherein the plate comprises a midsection between the first and second ends of the plate, the midsection comprising a third elongated slot having a long axis and a short axis, the third elongated slot having a seat portion and a slot configuration identical to the first and second elongated slots.

5. The fixation plate system of claim 4, wherein the third elongated slot comprises a pair of elongated slots extending parallel to one another at the midsection of the plate.

6. The fixation plate system of claim 4, wherein the plate comprises a window between the first and third elongated slots, or between the second and third elongated slots.

7. A fixation plate system comprising:
- an elongated plate having a first end, a second end and a longitudinal axis extending from the first end to the second end, the first end comprising a first elongated slot having a long axis and a short axis, the second end comprising a second elongated slot having a long axis and a short axis, the first and second elongated slots each having a seat portion, the short axis of the first elongated slot equal in length to the short axis of the second elongated slot;
- a semi-constrained fastener having a radially expandable head and a shank, the head of the semi-constrained fastener comprising a plurality of elastically deformable petals, the shank of the semi-constrained fastener being received through the first elongated slot and the head of the semi-constrained fastener positioned in the seat portion of the first elongated slot with the elastically deformable petals of the semi-constrained fastener engaging the seat portion in an interference fit to inhibit translation of said head within the first elongated slot; and
- a dynamic fastener having a radially expandable head and a shank, the head of the dynamic fastener comprising a plurality of elastically deformable petals, the shank of the dynamic fastener being received through the second elongated slot and the head of the dynamic fastener positioned in the seat portion of the second elongated slot with the elastically deformable petals of the dynamic fastener engaging the seat portion in a non-interference fit to allow translation of said head within the second elongated slot,
- the diameter of the head of the semi-constrained fastener being greater than the diameter of the head of the dynamic fastener such that the head of the semi-constrained fastener is positioned in the seat portion of the first elongated slot in an interference fit to inhibit translation of said head within the first elongated slot, and the head of the dynamic fastener is positioned in the seat portion of the second elongated slot in a non-interference fit to allow translation of said head within the second elongated slot.

8. The fixation plate system of claim 7, wherein the semi-constrained fastener is selectively insertable into either the first elongated slot or the second elongated slot in an interference fit to attach the plate to a first vertebra and restrict motion of the plate relative to the first vertebra.

9. The fixation plate system of claim 7, wherein the dynamic fastener is selectively insertable into either the first elongated slot or the second elongated slot in a non-interference fit to attach the plate to a second vertebra and allow translation of the plate relative to the second vertebra.

10. The fixation plate system of claim 7, wherein the head of the semi-constrained fastener is larger than the head of the dynamic fastener.

11. The fixation plate system of claim 10, wherein the shank of the semi-constrained fastener is received through a middle area of the first elongated slot, and the shank of the dynamic fastener is received through an end area of the second elongated slot.

12. The fixation plate system of claim 11, wherein the shank of third fastener is received through a middle area of the third elongated slot.

13. The fixation plate system of claim 7, wherein the long axis of the second slot is greater than the long axis of the first slot.

14. The fixation plate system of claim 7, wherein the plate comprises a midsection between the first and second ends of the plate, the midsection comprising a third elongated slot having a long axis and a short axis, the third elongated slot having a seat portion.

15. The fixation plate system of claim 14 comprising a third fastener having a head and a shank, the shank of the third fastener being received through the third elongated slot and the head of the third fastener positioned in the seat portion of the third elongated slot in an interference fit to inhibit translation of said head within the third elongated slot.

16. The fixation plate system of claim 14, wherein the plate comprises a bend through the midsection such that the first elongated slot has a planar orientation that is different than a planar orientation of the second elongated slot.

17. The fixation plate system of claim 14, wherein the third fastener is a dynamic screw.

18. The fixation plate system of claim 14, wherein the dimensions of the first elongated slot are identical to the dimensions of the third elongated slot.

* * * * *